United States Patent
Triantafyllou

(10) Patent No.: US 6,592,914 B1
(45) Date of Patent: Jul. 15, 2003

(54) METHOD FOR ISOLATION OF A β-GLUCAN COMPOSITION FROM OATS AND PRODUCTS MADE THEREFROM

(76) Inventor: Angeliki Oste Triantafyllou, Kollegievagen 91, S-224 73 Lund (SE)

( * ) Notice: Subject to any disclaimer, the term of this patent is extended or adjusted under 35 U.S.C. 154(b) by 0 days.

(21) Appl. No.: 09/660,424

(22) Filed: Jun. 30, 2000

Related U.S. Application Data

(63) Continuation of application No. 09/179,107, filed on Oct. 26, 1998, now abandoned.

(51) Int. Cl.$^7$ .................... A23L 1/0522; A23L 1/09; A23L 1/105
(52) U.S. Cl. .............. 426/28; 426/52; 426/384; 426/469; 426/472; 426/661; 536/127; 536/128; 536/523.12
(58) Field of Search ............... 426/28, 52, 661, 426/469, 472, 384; 536/523.12, 127, 128

(56) References Cited

U.S. PATENT DOCUMENTS

| | | | |
|---|---|---|---|
| 4,996,063 A | | 2/1991 | Inglett |
| 5,380,542 A | * | 1/1995 | Jenkins et al. ............... 426/28 |
| 5,395,640 A | * | 3/1995 | Harris et al. ................. 426/28 |
| 5,616,355 A | | 4/1997 | Haast et al. |
| 5,633,369 A | * | 5/1997 | Jamas et al. ........... 536/123.12 |
| 5,686,123 A | * | 11/1997 | Lindahl et al. .............. 426/28 |

FOREIGN PATENT DOCUMENTS

| | | |
|---|---|---|
| EP | 0231729 | 8/1987 |
| WO | 94/28742 | 12/1994 |
| WO | 95/07628 | 3/1995 |

* cited by examiner

*Primary Examiner*—Helen Pratt
(74) *Attorney, Agent, or Firm*—Dickstein, Shapiro, Morin & Oshinsky, LLP.

(57) ABSTRACT

A method for producing, from an oats flour fraction, a water soluble β-glucan composition having a high β-glucan/glucose weight ratio, preferably a ratio of 15:1 or more, involves the use of β-amylase in an amount sufficient to transform more than 50% by weight, preferably more than 65% by weight, of the starch contained in the oats flour fraction to maltose. The enzymes pullulanase and/or protease may be used in combination with β-amylase. Also disclosed are corresponding compositions which may be further processed, as well as food products provided with them.

21 Claims, 1 Drawing Sheet

METHOD FOR ISOLATION OF A β-GLUCAN COMPOSITION FROM OATS AND PRODUCTS MADE THEREFROM

This a continuation of application Ser. No. 09/179,107, filed Oct. 26, 1998, now abandoned.

BACKGROUND OF THE INVENTION

The present invention relates to a method for the isolation of a water soluble native β-glucan composition from oats, to the corresponding composition as such, and to products prepared from this composition.

Water soluble native β-glucan is of major nutritional interest. It is the chemical constituent of 'soluble dietary fiber', SDF, considered to be responsible for the association between oats products and reduced risk for coronary heart disease. In this context the term 'native' indicates that the carbohydrate has not been degraded enzymatically to a substantial extent during its isolation. A variety of health food products rich in SDF are currently on the market.

Barley and oats are rich in SDF. Oats SDF is documented as being particularly healthy.

A method for making a SDF composition from oats is disclosed in U.S. Pat. No. 4,996,063 (Inglett). The method of Inglett comprises gelatinizing a milled oat substrate prior to treating it with an α-amylase which may yield substantial amounts of glucose. From the hydrolyzed mixture, an aqueous SDF fraction is recovered by separating water insoluble material. The usefulness of the β-glucan product produced by the method of U.S. Pat. No. 4,996,063 as a food additive is however diminished by its high glucose content. A high content of glucose promotes the formation of undesired, that is, colored and bitter products on heating in the presence of amino acids (Maillard reaction). Moreover the Maillard reaction preferentially consumes lysine which is an amino acid essential to man. In many aplications a high glucose content is a drawback because of the sweetness of glucose.

In the context of producing and further handling SDF, it is important to prevent the action of β-glucanase possibly present to avoid β-glucan degradation which would ensue in loss of nutritional value. It is also important to provide the β-glucan product essentially free of β-glucanase.

The production of pure and stable SDF from oats is hampered by its rather high content of fat, proteins and, in particular, β-glucanase.

SUMMARY OF THE INVENTION

It is an object of the present invention to provide a method of the aforementioned kind enabling the production of a stable, high yield β-glucan composition from oats.

It is another object of the invention to provide a method for the production of a stable, high yield, water soluble β-glucan composition from oats which has low sweetness and high temperature stability under conditions of food preparation and food processing.

It is a further object of the present invention to provide corresponding compositions and products prepared from them.

According to the invention is disclosed a method for producing, from an oats flour fraction, a water soluble β-glucan composition having a high β-glucan/glucose weight ratio, preferably a ratio of 15:1 or more, the method comprising the use of β-amylase in an amount sufficient to transform more than 50% by weight, preferably more than 65% by weight, of the starch contained in the oats flour fraction to maltose. In addition substantial amounts of water soluble oligosaccharides are formed.

It is preferred for the method according to the invention to comprise, in addition to the use of β-amylase, the use of pullulanase which 'promotes' the action of β-amylase. Pullulanase is a starch debranching enzyme which also aids saccharification to disaccharides and maltose as the dominating monosaccharide while not promoting the formation of glucose.

According to an advantageous aspect of the invention, it is preferred for the method according to the invention to additionally comprise the use of protease. This is particularly advantageous if a purification of the β-glucan composition of the invention to increase its content of water soluble β-glucan is contemplated.

According to another advantageous aspect of the invention, it is preferred for the method of the invention to comprise the use of (in terms of enzymatic activity in relation to β-amylase) α-amylase in an amount capable to accelerate the starch degradation process but not to form substantial amounts of glucose. It is preferred to add from 0 to 10%, more preferred from 1 to 5%, of α-amylase in terms of enzymatic activity relative to β-amylase. The person skilled in the art will realize that the amount of α-amylase needed for this end will vary according to reaction conditions (time, temperature, etc.) but can be easily determined by simple experimentation.

In particular, the method of the invention comprises the following steps:

- selecting an oats variety rich in β-glucan and, optionally, low in fat;
- producing oats flour by dry-milling of said oats variety;
- selecting an oats flour fraction rich in β-glucan by sieving or other particle size/weight discriminating means;
- adding to an aqueous medium the flour fraction which had been heat-treated as such or prepared from a heat treated oats variety or from heat-treated oats flour, β-amylase and, optionally, pullulanase;
- adding to an aqueous medium the thus treated flour fraction, β-amylase and, optionally, pulullanase;
- heating the thus produced suspension at a temperature above 30° C. for a time period sufficient to substantially degrade starch;
- inactivating added enzymes by further heating of the suspension and/or by other means;
- forming a water soluble β-glucan composition by removing water insoluble material;
- optionally, concentrating and/or drying said β-glucan composition.

It is preferred for the temperature at which the suspension is heated to degrade most of the starch and proteins to be from 52° C. to 65° C., in particular about 55° C.

The temperature at which the suspension is heated to inactivate the added enzymes is preferably from about 80° C. to about 95° C.

It is preferred to form the water soluble β-glucan composition by removing water insoluble material by centrifugation and/or filtration.

The β-glucan composition of the invention may be used in form of its aqueous solution which, at higher concentrations, turns into a gel at room temperature, or in form of a powder obtained by, for instance, freeze or spray drying of aqueous solutions of the β-glucan composition.

The β-glucan composition of the invention can be used as a food additive, for instance as an additive of soft drinks and beer, the latter use being particularly preferred.

According to an advantageous aspect, the β-glucan composition of the invention can be treated with a protease, in particular Alkalase®, to degrade proteins to peptides and amino acids. This is particularly advantageous if removal of low-molecular weight compounds, for instance of compounds having a molecular weight of below 200, is contemplated. Apropriate methods for removal of low-molecular weight constituents include ultra-filtration, reverse osmosis, and gel filtration. It is also within the scope of the invention to add such enzymes prior or during the formation of the β-glucan composition of the invention, for instance during the starch degradation step of the method of the invention.

The present invention also discloses food products enriched with the β-glucan product of the invention. Enriched liquid products include fruit juices, beer, mash, milk and fermented liquid and semi-liquid dairy products, milk and cream substitutes, soft drinks, syrups, liquid honey, etc.

The β-glucan product of the invention may also be used as a gelling additive in various food products. The freeze dried product is particularly suited as additive to solid or essentially solid food products, like bread, biscuits, chips, etc.

Further advantages of the invention are disclosed in the claims and will also be evident from a preferred, not limiting embodiment of the invention described in the following in greater detail by reference to a single Figure showing a chart illustrating the process the invention.

DETAILED DESCRIPTION OF THE PREFERRED EMBODIMENT

Figure 1:
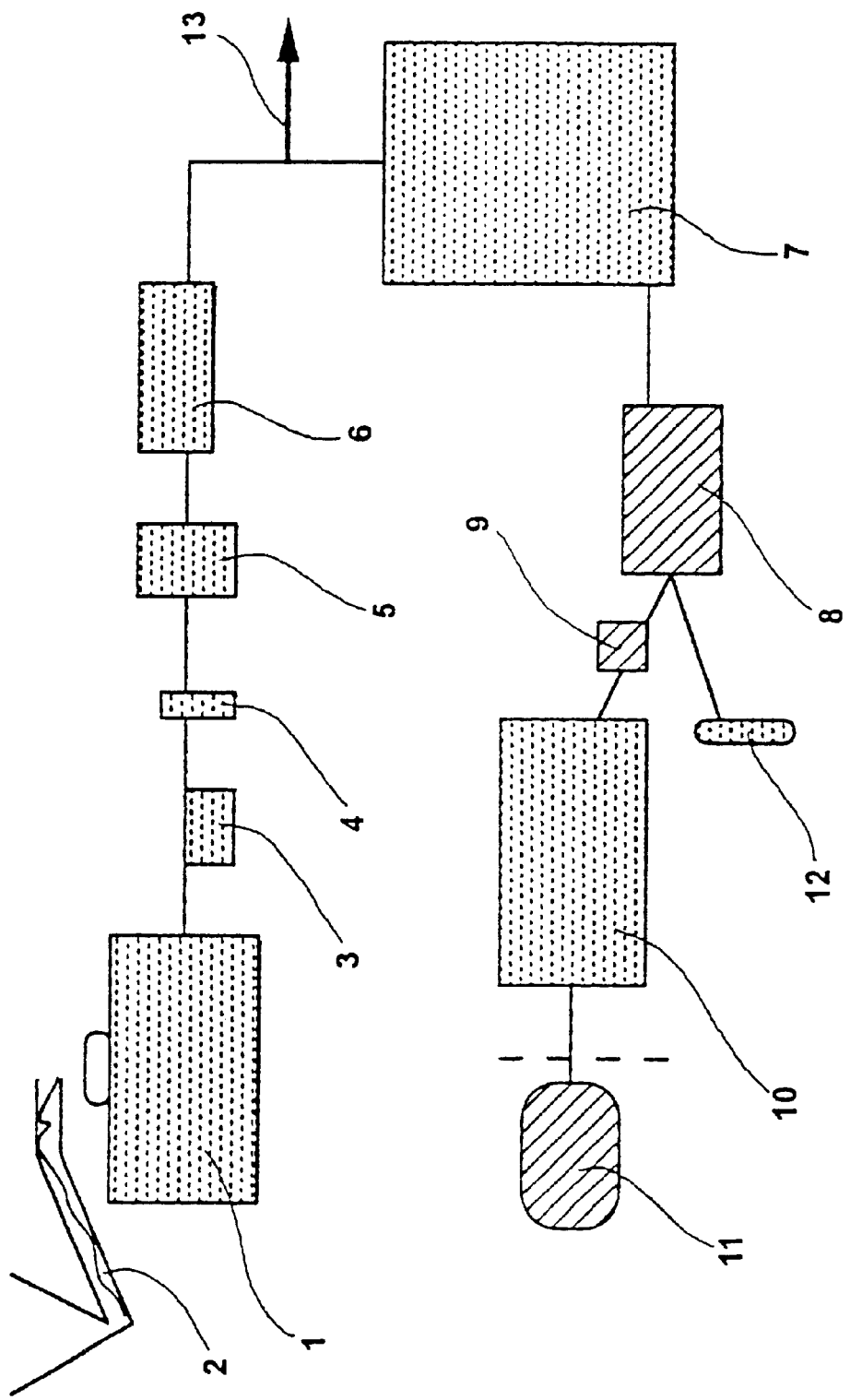
FIG. 1 illustrates an apparatus and process for producing a beta glucan composition according to an exemplary embodiment of the present invention.

Materials. A commercial heat-treated oats flour fraction high in β-glucan, 'HAVREMJÖL C45', was obtained from Skåne-möllan (Tågarp, Sweden). Oats flour fractions high in β-glucan can be also be obtained by applying the teaching of U.S. Pat. No. 5,063,078 (Frohse) to oats. β-Amylase was obtained from Genencor International, Inc. (Rochester, N.Y., USA). α-Amylase, pullulanase and protease, for example Alcalase®, were obtained from Novo Nordisk, (Valby, Denmark).

Enzymatic degradation of starch and, optionally, protein. To a thermostat-controlled, heat-mantled 100 l stainless steel tank 1 provided with an efficient stirrer containing 30 l of water at 55° C. is added 54 g of β-amylase and 18 g of pullulanase. Then 6 kg of heat treated oat meal is added by a screw feeder 2 within 20 minutes so as to keep the viscosity below 128 mPas at a shear rate of 697 s$^{-1}$. The suspension is heated under stirring at 55° C. The viscosity of the suspension is monitored by a Bohlin Visco 88 meter. The dry matter content of the suspension thus reaches about 20%.

After 2 hrs the viscosity drops to 40 mPas at a shear rate of 697 s$^{-1}$. Then 5 g of Alcalase® is added and heating at 55° C. is continued for another 30 minutes. Via a balance vessel 3 the suspension is pumped to a steam injector 4 in which its temperature is raised to 90° C. to inactivate added enzymes. From there the suspension is cooled, preferably to a temperature below 40° C., for instance by pumping it through a heat exchanger 5 in which it is brought to room temperature, and further to a decanter centrifuge 6 (5,000 rpm) for separation of remaining solids (at 13; about ⅓ by weight of solids at start) which may be used, for instance, for the production of animal foodstuff.

The clear solution thus obtained contains about 2% of native soluble β-glucan. The β-glucan solution is collected in a collection tank 7 from which it is discharged in portions and transported to a pasteurization station 8. After passing station 8 it is cooled to ambient temperature in a heat exchanger 9 and stored in a storage tank 10 from which it can removed for additional treatment, such as evaporation in an evaporator 11 to produce a highly viscous gel or freeze-drying to yield a porous powder containing 17% by weight of β-glucan. Alternatively the pasteurized solution can be discharged from the storage tank 10 for packaging 12 and transport to other sites to be used as such. If desired the solution can be purified by removing low molecular constituents, mainly hydrolysis products of starch and proteins, by ultra-filtration.

What is claimed is:

1. A method for producing a solution of a water soluble β-glucan composition having a high β-glucan/glucose weight ratio from an oats flour fraction, the method comprising:

β-amylase catalyzed enzymatically transforming, in an aqueous medium, more than 50% by weight of the starch contained in the oats flour fraction to maltose; and removing remaining water insoluble material to obtain a water soluble β-glucan composition having a β-glucan/glucose weight ratio of at least 15:1.

2. The method of claim 1, comprising β-amylase catalyzed enzymatically transforming more than 65% by weight of the starch contained in the oats flour fraction to maltose.

3. The method of claim 1, comprising conducting the β-amylase catalyzed enzymatically transforming in the presence of pullulanase or protease or both.

4. The method of claim 1, comprising additionally employing α-amylase in an amount so as to essentially avoid the formation of glucose, while promoting the activity of β-amylase.

5. The method of claim 4, wherein the amount of α-amylase is up to 10% of the enzymatic activity of β-amylase.

6. The method of claim 5, wherein the amount of α-amylase is 1 to 5% of the enzymatic activity of β-amylase.

7. A method for producing an aqueous solution of a water soluble β-glucan composition from oats which has a high β-glucan/glucose weight ratio, the method comprising the steps of:

selecting at least one member of the group consisting of (a) an oats variety rich in β-glucan and optionally low in fats (b) an oats flour comprising said oats variety dry-milled and (c) a fraction of said oats flour rich in β-glucan;

inactivating carbohydrate degrading enzymes in said selected member to obtain an inactivated member;

dry milling the resulting inactivated member to obtain a milled member;

combining said milled member with an aqueous medium and β-amylase and, optionally, β-pullulanase, to form a suspension;

heating the thus produced suspension at a temperature above 30° C. for a time period sufficient to substantially degrade more than 50% of the starch to maltose as the dominating disaccharide;

inactivating said added β-amylase and, when present, pullulanase enzymes; and removing remaining water insoluble material to form an aqueous solution of a water soluble β-glucan.

8. The method of claim 7, wherein the temperature at which the suspension is heated to degrade starch is from 52° C. to 65° C.

9. The method of claim 7, wherein the temperature at which the suspension is heated to degrade starch is about 55° C.

10. The method of claim 7, wherein the temperature at which the suspension is heated to inactivate enzymes is from about 80° C. to about 95° C.

11. The method of claim 7, wherein the water insoluble material is removed by centrifugation or filtration or both.

12. The method of claim 7, wherein the β-glucan composition is spray or freeze dried.

13. The method of claim 7, wherein low molecular weight compounds are removed from the β-glucan composition by ultra-filtration.

14. An aqueous β-glucan solution produced by the process of claim 1.

15. A food product containing the β-glucan solution of claim 14.

16. A beverage containing the β-glucan solution of claim 14.

17. The solution of claim 14 in which at least some of the poly-and oligosaccharides have been enzyme degraded to maltose, or at least some proteins have been enzyme degraded to peptides and amino acids, or both.

18. The solution of claim 17 having a reduced content of constituents having a molecular weight below 200.

19. An oats composition obtained by concentrating the solution of claim 14 and containing 10% by weight or more of water soluble β-glucan native to an original oats fraction.

20. The composition of claim 19, wherein the content of water soluble β-glucan is 15% by weight or more.

21. The composition of claim 19, wherein the concentrating is performed by freeze-drying.

* * * * *